United States Patent [19]
Yeo et al.

[11] Patent Number: 5,827,196
[45] Date of Patent: Oct. 27, 1998

[54] METHOD AND SYSTEM FOR PROVIDING CHARACTERIZATIONS OF WAVEFORM REPRESENTATIONS OF HEART FUNCTION

[75] Inventors: Cheuw Lee Yeo, Andover; Jyh-yun J. Wang, Newton, both of Mass.

[73] Assignee: Hewlett-Packard Company, Palo Alto, Calif.

[21] Appl. No.: 893,115

[22] Filed: Jul. 15, 1997

[51] Int. Cl.$^6$ .................................................. A61B 5/0402
[52] U.S. Cl. .......................................... 600/509; 128/901
[58] Field of Search ............................ 128/901; 600/509, 600/521; 607/27

[56] References Cited

U.S. PATENT DOCUMENTS

| | | | |
|---|---|---|---|
| 4,751,931 | 6/1988 | Briller et al. | 600/509 |
| 4,987,901 | 1/1991 | Kunig | 600/509 |
| 5,685,315 | 11/1997 | McClure et al. | 600/521 |

*Primary Examiner*—William E. Kamm
*Assistant Examiner*—Kennedy J. Schaetzle

[57] ABSTRACT

A method and system for providing highly accurate characterizations of waveform representations of heart function, such as QRS complexes, where such waveform representations are derived from electrocardiographic measurements. The method and system accomplish their objects via the following. One or more signals indicative of heart function are measured and sampled. One or more signal quality indexes are calculated for each of the measured and sampled one or more signals. The signal quality indexes are calculated by dividing a maximum sample value for each one or more measured and sampled signal by a calculated divisor. One or more weighting factors, dependent upon the calculated signal quality index of each of the one or more measured and sampled signals are calculated. And, a waveform representation composed of each of the one or more measured and sampled signals indicative of heart function multiplied by its calculated weighting factor is created.

24 Claims, 8 Drawing Sheets

METHOD AND SYSTEM FOR PROVIDING CHARACTERIZATIONS OF WAVEFORM REPRESENTATIONS OF HEART FUNCTION

BACKGROUND

1. Technical Field

The present invention relates, in general, to a method and system for providing highly accurate characterizations of waveform representations of heart function, such as QRS complexes. In particular, the present invention relates to a method and system for providing highly accurate characterizations of waveform representations of heart function, such as QRS complexes, where such waveform representations are derived from electrocardiographic measurements.

2. Description of Related Art

The present invention presents a method and system for automatically producing highly accurate characterizations of waveform representations of heart function, such as QRS complexes, where such waveform representations are constructed from electrocardiographic measurements. The present invention produces such highly accurate characterizations of waveform representations by (1) providing an innovative way of analyzing each member of a set of electrocardiographic measurements that are ultimately to be used to construct the waveform representation in order to determine if the member analyzed is a good or poor representation of heart function, and (2) thereafter utilizing only those signals which such analysis determined were good to construct the characterization of waveform representation.

One illustrative embodiment of the present invention utilizes certain specific electrical signals derived from a device for monitoring heart function known as the electrocardiograph. In order to understand how these certain specific electrical signals are utilized, it is helpful to have a basic understanding of the electrocardiograph and to what the certain specific electrical signals refer. Accordingly, as an aid to understanding the electrocardiograph, the discussion below presents a brief description of (1) the electrochemical and mechanical operation of the heart, (2) how the electrochemical operation of the heart is transduced into electrical energy which is then used by the electrocardiograph to graphically denote the mechanical operation of the heart, and (3) how the certain specific electrical signals (or "leads") are derived from the electrocardiograph.

The mechanical events of the heart are preceded and initiated by the electrochemical activity of the heart (i.e., the propagation of the action potential). There is a device which transforms the electrochemical activity of the heart into a form visible to the human eye: the electrocardiograph, which produces a visual representation of the electrochemical activity of the heart. The visual representation is known as the electrocardiogram (EKG).

During an EKG, electrodes are attached to the body surface. The electrodes are specially treated to allow the charge carriers within the electrodes (electrons) to communicate with the charge carriers within the body (ions) via electrochemical exchange. Attaching electrodes to the body surface allows the voltage changes within the body to be recorded after adequate amplification of the signal. A galvanometer within the EKG machine is used as a recording device. Galvanometers record potential differences between two electrodes. The EKG is merely the recording of differences in voltage between two electrodes on the body surface as a function of time, and is usually recorded on a strip chart. When the heart is at rest, diastole, the cardiac cells are polarized and no charge movement is taking place. Consequently, the galvanometers of the EKG do not record any deflection. However, when the heart begins to propagate an action potential, the galvanometer will deflect since an electrode underneath which depolarization has occurred will record a potential difference from a region on the body under which the heart has not yet depolarized.

A complete heart cycle is known as a heartbeat. On an EKG, a normal heartbeat has a distinctive signal. Initially, the galvanometer notes a relatively short duration rounded positive deflection (known as the P wave), which is caused by atrial depolarization. Subsequent to this, there is a small but sharp negative deflection (known as the Q wave). Next, there is a very large and sharp positive deflection (known as the R wave), after which there is a sharp and large negative deflection (known as the S wave). When these waves are taken together, they are known as the QRS complex. The QRS complex is caused by ventricular depolarization. Subsequent to the QRS complex, is a relatively long duration rounded positive deflection (known as the T wave), which is caused by ventricular repolarization.

The EKG, in practice, uses many sets of electrodes. But these electrodes are so arranged on the surface of the body such that the signal received will have the similar shape as that just described. Well-known bipolar pairs of electrodes are typically located on a patient's right arm (RA), left arm (LA), right leg (RL) (commonly used as a reference), and left leg (LL). Monopolar electrodes referenced properly are referred to as V leads and are positioned anatomically on a patient's chest according to an established convention (labeled as follows as Leads V1–V6). In heart monitoring and diagnosis, the voltage differential appearing between two such electrodes or between one electrode and the average of a group of other electrodes represents a particular perspective of the heart's electrical activity and is generally referred to as the EKG. Particular combinations of electrodes are called leads. For example, the leads which may be employed in a standard twelve-lead electrocardiogram system are:

Lead I=(LA−RA)
Lead II=(LL−RA)
Lead III=(LL−LA)
Lead V1=V1−(LA+RA+LL)/3
Lead V2=V2−(LA+RA+LL)/3
Lead V3=V3−(LA+RA+LL)/3
Lead V4=V4−(LA+RA+LL)/3
Lead V5=V5−(LA+RA+LL)/3
Lead V6=V6−(LA+RA+LL)/3
Lead aVF=LL−(LA+RA)/2
Lead aVR=RA−(LA+LL)/2
Lead aVL=LA−(RA+LL)/2

Thus, although the term "lead" would appear to indicate a physical wire, in electrocardiography the term actually means the electrical signal taken from a certain electrode arrangement as illustrated above.

Over the years, health care professionals have built up a body of knowledge wherein they have learned to correlate variations in the EKG with different diseases and heart defects. Formally, this process of correlating is known as "electrocardiography."

Electrocardiography, as practiced by human cardiologists, is primarily a visually oriented art in that the human cardiologists visually inspects a waveform tracing of electrocardiographic measurements taken over time, and on the basis of the morphological (i.e., shape) changes of the waveform over time the human cardiologist makes a diagnosis of heart function. In making such diagnosis, it is essential that the human cardiologist have an accurate characterization (e.g., knowledge of where the QRS complex appears) of waveform representation, derived from the electrocardiographic measurements, of heart function in that inaccuracies in the waveform will give rise to inaccuracies in diagnosis.

The requirement for an accurate characterization (e.g., where the QRS complex is located) of waveform representation is even more critical for mechanized electrocardiography. That is, machines have been created which have automated many of the functions traditionally performed by human cardiologists. One of the most common ways by which engineers have been able to create these machines has been to approximate the diagnoses of the human cardiologists via the use of one or more waveform templates as a baseline against which a patient's waveform representation of heart function is compared.

The way in which such templates are typically used is as follows. First, a multi-lead electrocardiograph is affixed to a particular patient and an electrocardiogram is begun. Second, an EKG waveform is obtained from one or more leads. Third, one or more waveform templates indicative of certain heart conditions of interest are cross correlated with the patient's stored waveform. The waveform template is cross correlated with the patient's EKG waveform by "sweeping" the waveform template over the received waveform and keeping track of how well the waveform template intersected with the patient's EKG waveform. If it is determined that the base template correlated well with the patient's received data, then it is determined that the patient has the heart condition associated with the template.

In order for such correlation techniques to give accurate diagnosis, it is important that the characterization (e.g., where the QRS complex is located) of the patient's EKG waveform (a waveform representation of heart function) be as accurate as possible. Such is important because such correlation techniques often diagnose on the morphological differences and or similarities between the shape of certain EKG features (e.g., the QRS complex within EKG data) within a patient's EKG waveform and the templates correlated against the patient's EKG waveform. Again, as for human cardiologists, it is critical that the mechanized cardiologist have an accurate characterization (e.g., where the QRS complex is located) of the waveform representation, derived from the electrocardiographic measurements, of heart function in that inaccuracies in the characterization of the waveform will often give rise to inaccuracies in diagnosis.

As noted, an accurate characterization (e.g., where the QRS complex is located) of patient EKG waveform data is very important for multiple reasons. However, such accurate characterization can be difficult to achieve because various EKG leads often produce "dirty" or distorted signals. These distortions can result from many factors, such as insufficient preparation of EKG electrodes which can result in poor electrical connection with the patient, and low frequency noise or high frequency noise arising from patient movement or muscle twitch. When such distorted signals are present it is often difficult to adequately characterize the EKG waveform representation because the one or more "dirty" or distorted signals make such characterization difficult. Yet, as has been discussed, in order for either a human cardiologist or a machine to utilize EKG data to produce accurate diagnosis of heart function, such accurate characterization of EKG waveforms is critical.

In previous attempts to provide accurate characterization of patient EKG waveform data based on multiple leads, the multiple leads are all combined first to form a single signal for QRS detection. The methods previously used to combine the multiple ECG signals include (1) summing the signals, or (2) multiplying the signals. However, summing the multiple leads is only useful for improving the signal-to-noise ratio of the combined signal when noise is present in a minority of the leads being processed. Furthermore, noise of sufficient magnitude in any single lead can adversely affect the final detection signal when summing is used. On the other hand, combining multiple leads by using a multiply function, while overcoming the previously noted problems surrounding summing, can create additional problems such as a false negative which may occur when any single lead has a QRS complex that is isoelectric.

It is apparent from the foregoing that multiple needs exist for the present invention: a method and system that provide highly accurate characterizations of waveform representations of heart function, such as QRS complexes, where such waveform representations are derived from electrocardiographic measurements.

SUMMARY OF THE INVENTION

It is therefore one object of the present invention to provide an improved method and system for providing highly accurate characterizations of waveform representations of heart function, such as QRS complexes.

It is another object of the present invention to provide a method and system for providing highly accurate characterizations of waveform representations of heart function, such as QRS complexes, where such waveform representations are derived from electrocardiographic measurements.

The foregoing objects are achieved as is now described. A method and system for providing highly accurate characterizations of waveform representations of heart function, such as QRS complexes, where such waveform representations are derived from electrocardiographic measurements. The method and system accomplish their objects via the following. One or more signals indicative of heart function are measured and sampled. One or more signal quality indexes are calculated for each of the measured and sampled one or more signals. The signal quality indexes are calculated by dividing a maximum sample value for each one or more measured and sampled signal by a calculated divisor. One or more weighting factors, dependent upon the calculated signal quality index of each of the one or more measured and sampled signals are calculated. And, a waveform representation composed of each of the one or more measured and sampled signals indicative of heart function multiplied by its calculated weighting factor is created.

The above as well as additional objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAILED DESCRIPTION OF PREFERRED EMBODIMENT

The following description describes a method and system which utilizes electrocardiographic measurements. The method and system are related to the provision of highly accurate characterizations of waveform representations of heart function, such as QRS complexes, where such waveform representations are constructed from electrocardiographic measurements.

It will be understood by those in the art that while electrocardiographic leads (i.e., signals) are analog, it is common to time sample each electrocardiographic lead. Accordingly, most of the discussion below deals with such discretely sampled signals; however, in some instances, conceptual clarity will be served in referring to the analog waveforms, and in such instances the discussion will treat the leads utilized by the present invention "as if" they were analog.

The present invention creates a characterization of waveform representation of heart function based upon electrocardiographic measurements. The waveform representation is produced by use of what is called an "Activity Function" in the present invention. The "Activity Function" is a composite of one or more individual electrocardiographic leads (signals). As will be shown below, the "Activity Function" gives an exceptionally accurate characterization of waveform representations of heart function, such as QRS complexes, because the one or more individual electrocardiographic leads ultimately utilized to construct the "Activity Function" are only those which have been (1) determined to exceed some defined baseline quantity representative of a "good" signal, and (2) have been "weighted" such that the "better" a signal is the more weight it is given to produce the ultimate construct of the "Activity Function." Accordingly, prior to discussing the Activity Function it is helpful to discuss how signal quality is assessed and how the weighting factors are based on that signal quality.

One of the facets of the present invention is an innovative way of assessing the signal quality of electrocardiographic leads (i.e., how to determine which leads are "good" quality signals). Electrocardiography is a primarily visual art, practiced by human cardiologists. That is, when a human cardiologist is presented with a set of, for example, twelve (12) electrocardiographic leads (signals), the human cardiologist will rank order the leads from best to worst quality on the basis of visual inspection. Such visual inspection is primarily subjective with the cardiologist. Hence, a major challenge in the art has been to devise a way to mechanically achieve what the human cardiologist does by inspection.

The present invention mechanistically achieves what the human cardiologist does by visual inspection by introducing a quantity referred to as a Signal Quality Index.

As discussed, in the present invention, the "goodness" of a signal is correspondent to its "Signal Quality Index." In general (except of special case instances, which will be defined later) the SQI for any particular $i^{th}$ lead is defined as follows:

$$SQI^{(i)} = \frac{\text{MAX}\{|V^{(i)}(j)|, j = n - 49, n\} \times 50}{\sum_{j=n-49}^{n} |V^{(i)}(j)|}$$

where:

$V^{(i)}(j)$ is the EKG value at the jth data sample for the ith lead;

i is the lead under consideration, and ranges from 1 to N where N is the total number of leads present;

j is the jth EKG data sample for lead i under consideration; and n is the leading edge sample time of the sample window over which SQI is computed (width of sample window is 50 samples, in the equation given).

The definition of SQI makes clear that the SQI is calculated for each lead present. In words, the equation states that the maximum absolute value occurring within each lead is determined over some time baseline wherein 50 samples are taken, this determined maximum absolute value is then multiplied by the number 50. The result of this multiplication is then divided by the sum of the EKG sample values of the lead that were taken over a window of 50 sample points.

Those skilled in the art will recognize that the foregoing equation could be used over any time base. However, by way of example, in one illustrative embodiment, the SQI is computed every 200 milliseconds over a window of 400 milliseconds (i.e, 50 8 millisecond data samples, or 50 data samples which were taken at 8 millisecond intervals). So, essentially the SQI is initially calculated over a 400 msec window composed of 50 equispaced data samples. Subsequently, the SQI is recalculated every 200 milliseconds, which means that the SQI is computed on 25 new samples and 25 previous samples (since the leading edge of the 400 millisecond wide sample window is only advanced 200 milliseconds before recomputation).

In addition, while the foregoing definition of SQI only dealt with 50 samples, those skilled in the art will understand that the foregoing SQI can conceivably be calculated over any baseline with any number of samples.

As discussed, the "Activity Function" is composed of only "good" signals, and the composition of the "Activity Function" is produced by weighting the qualitatively "better" signals such that their contribution to the Activity Function is greater than that of "poorer" quality signals. Hence, the weighting factors are dependent upon the assessed "goodness" or signal quality of different leads. This relation is made explicit by the following definition of the weighting factor, which clearly shows that the weighting factor is dependent upon signal quality, or SQI:

$$W^{(i)} = \frac{SQI^{(i)}}{\sum_{i=1}^{N} SQI^{(i)}} \quad i = 1, 2, \ldots N$$

-continued $$\text{unless } SQI^{(i)} = 0 \text{ for } i = 1, 2, \ldots N$$

$$\text{which causes } W^{(i)} = \frac{1}{N} \text{ for all } i$$

Where:

i is the lead under consideration;

$SQI^{(i)}$ is the signal quality index of the ith lead; and

N is the total number of EKG leads present;

Thus, the foregoing weighting factor equation generally holds except for the following defined exception (whose utility will become apparent later).

With the SQI and Weighting Factor equations now defined, the "Activity Function" is defined to be the following which is calculated on a sample by sample basis:

$$AF(k) = \sum_{i=1}^{N} W^{(i)} |V^{(i)}(k)|$$

where:

k is the kth EKG data sample;

$W^{(i)}$ is the weighting factor for the ith lead;

N is the total number of EKG leads; and $V^{(i)}(k)$ is the EKG value at the kth data sample for the ith lead.

It will be understood in the art that waveform representations of heart function, such as QRS complexes, can be utilized even when rectified (i.e., that polarity isn't important), which is why the "Activity Function" can utilize the absolute value of the samples.

Figure 1:
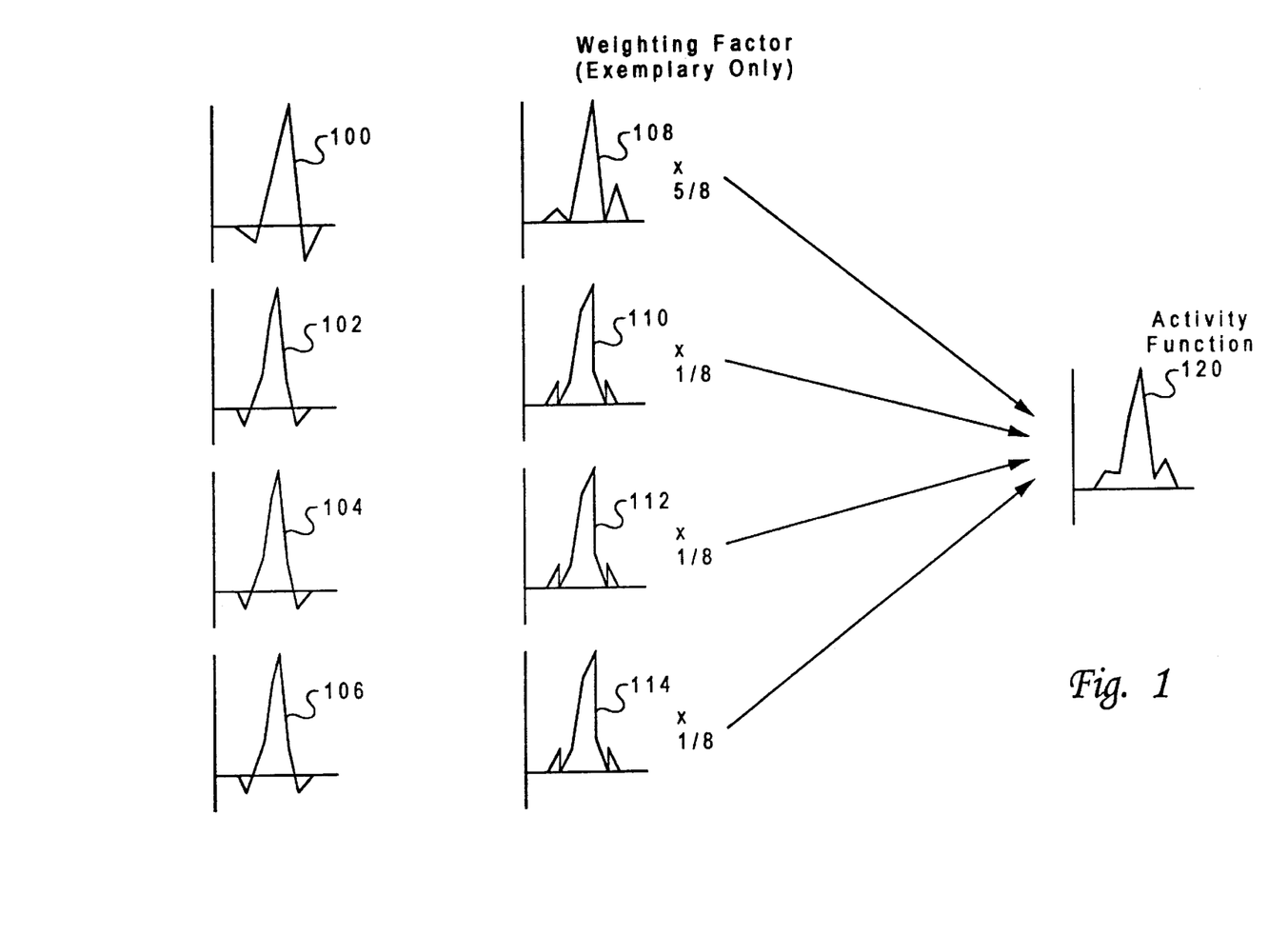
FIG. 1 is a partially schematic diagram illustrating concepts involved in the activity function.

Refer now to FIG. 1, which is a partially schematic diagram illustrating concepts involved in the Activity Function. Shown in FIG. 1 are four exemplary electrocardiographic signals (leads). Electrocardiographic signal 100 is an idealized QRS complex. Electrocardiographic signals 102, 104, and 106 are also QRS complexes, but are illustrated to represent less than ideal QRS complexes.

The Activity Function utilizes the absolute value of electrocardiographic signals. Accordingly, shown in FIG. 1 are rectified versions 108, 110, 112, and 114 of the four electrocardiographic signals 100, 102, 104, and 106, respectively.

As has been discussed above, the Activity Function utilizes weighting functions in conjunction with electrocardiographic signals to produce a composite function wherein the "best" electrocardiographic waveform makes the greatest contribution. Accordingly, shown in FIG. 1 is that rectified QRS complex 108 (equating to the idealized QRS complex 100, which is the "best" or "cleanest" waveform), is assigned a weighting factor of ⅝ (the weighting factors shown herein are merely presented to illustrate the concepts involved, and are not actual weighting functions derived from the signals shown). Furthermore, rectified QRS complexes 110, 112, and 114 (equating to QRS complexes 102, 104, and 106, respectively) are each assigned weighting factors of ⅛.

The rectified QRS complexes shown are then all multiplied by their respective weighting factors and summed (as per the Activity Function discussed above) to create the composite QRS complex 120. It can be seen from the composite QRS complex (i.e., Activity Function) that the composite QRS complex has been formed, in major part, by the "best" or "cleanest" QRS complex 100. Thus, FIG. 1 shows pictographically that the present invention gives a highly accurate representation of electrocardiographic waveforms because such representation is composed such that the waveforms with the "best" or "cleanest" signals are given the most weight.

As discussed above, in the present invention the assessed "goodness" of any particular lead (i.e., the signal quality) is determined via the use of the "Signal Quality Index," or "SQI." In the present invention, the SQI is generally computed for each lead present over a certain time base, utilizing a fixed number of samples taken over that time base. However, in the present invention there are special cases that are checked for prior to computing the "SQI." These special cases are used to determine whether the ordinary way in which SQI is calculated should be modified due to the fact that one or more of the leads manifests a particularly unsatisfactory signal. As will be shown below, if it is determined that a signal is particularly unsatisfactory, such signal will be assigned a predefined SQI rather than having one calculated for it.

The first special case that is checked is that where every lead manifests as a weak signal. In such a case, the SQI equation, given above, is disregarded, and instead the SQI for each and every lead is assigned a value of zero. Recall from above that it was defined that if all the signal quality indexes of leads present is found to be zero (i.e., $SQI^{(i)}=0$ for i=1 to N (where N equals all leads present) then the weighting factor is defined to be $W^{(i)}=1/N$ for i=1 to N (where N equals all leads present)). In other words, in the present invention, if all leads are found to be weak or unsatisfactory, then the signal index for each lead is assigned a value of zero, which ultimately results in equal weight being given to each signal.

That is, in such a case all leads are weighted equally. In one illustrative embodiment, the explicit criteria by which it is determined if every lead is manifesting as a weak signal is the following:

if $\text{MAX}\{|V^{(i)}(j)|, j=n-49, \ldots n\} \leq 250 \, \mu V$ for all N leads then set $SQI^{(i)}=0$ i=1, \ldots, N where:

i is the lead under consideration, and ranges from 1 to N where N is the total number of leads present;

j is the jth EKG data sample for lead i under consideration;

n is the leading edge sample time of the sample window over which SQI is computed (width of sample window is 50 samples, in the equation given); and $V^{(i)}(j)$ is the EKG value at the jth data sample for the ith lead.

In words, the equation says that if the maximum sampled value taken within some 50 sample block of every single lead is less than or equal to 250 microvolts, then it is determined that every single lead is manifesting as low amplitude, or weak signals. Accordingly, in such a situation the SQIs for all leads is set to zero, which ultimately results in the weighting factors are all being set to be 1/N for each lead, where N is the total number of leads.

Figure 2:
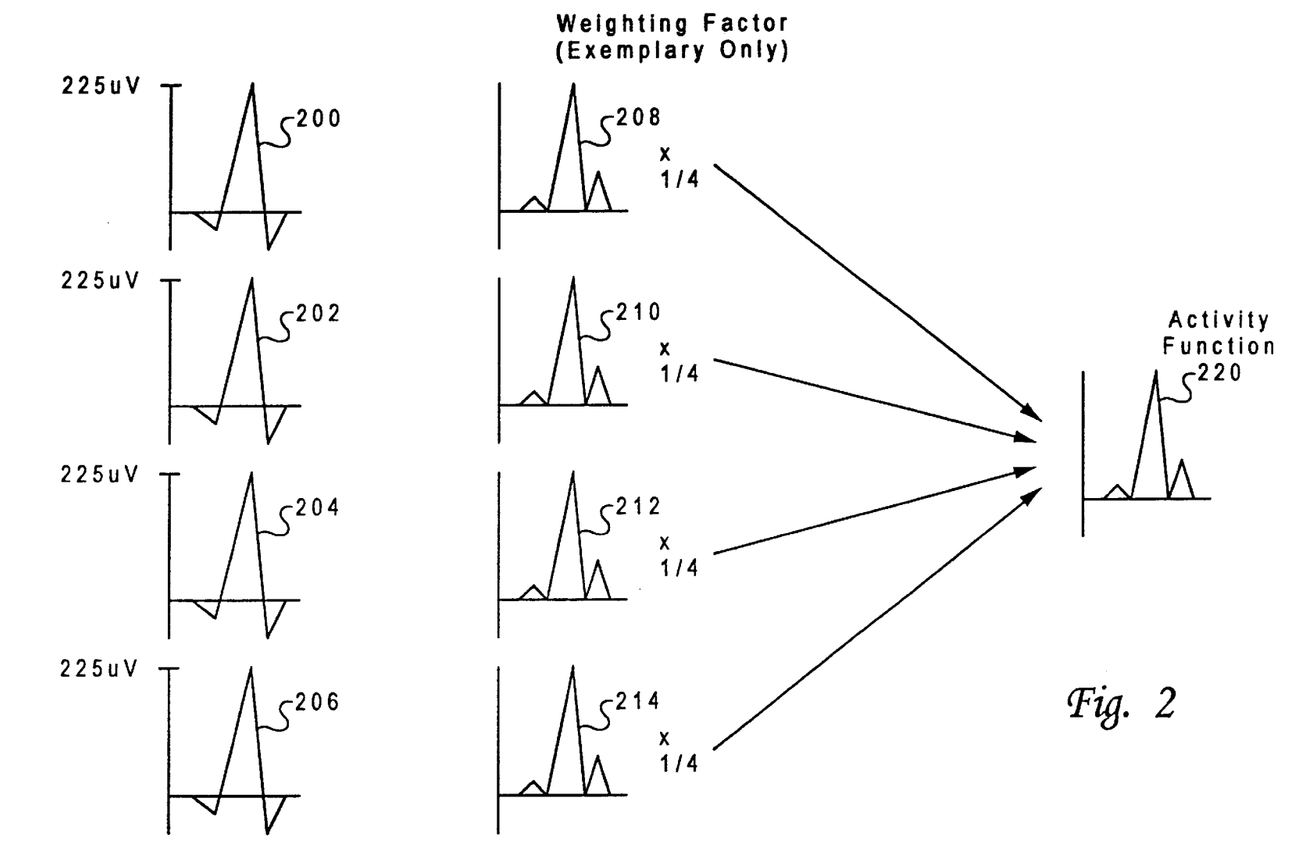
FIG. 2 is a partially schematic diagram illustrating concepts involved in the special case where all of the signals are weak.

Refer now to FIG. 2, which is a partially schematic diagram illustrating concepts involved in the special case where all of the signals are weak. Shown in FIG. 2 are four exemplary electrocardiographic signals (leads). Electrocardiographic signals 200, 202, 204, and 206 are all QRS complexes, but are illustrated to represent that the magnitudes of all components of the QRS complexes are less than 250 microvolts.

The Activity Function utilizes the absolute value of electrocardiographic signals. Accordingly, shown in FIG. 2 are rectified versions 208, 210, 212, and 214 of the four electrocardiographic signals 200, 202, 204, and 206, respectively.

As has been discussed above, in the special case shown in FIG. 2, where all electrocardiographic signals are "weak," the SQI for each lead is assigned a value of zero. Furthermore, as has also been discussed, in the case where the SQI of all leads is zero, the weighting function assigns a weighting factor of 1/N to all leads, where N is the total number of leads present. Accordingly, shown in FIG. 2 is that rectified QRS complexes 208, 210, 212, and 214 (equating to QRS complexes 200, 202, 204, and 206, respectively) are each assigned weighting factors of ¼, since there are 4 (i.e., N=4) leads present.

The rectified QRS complexes shown are then all multiplied by their respective weighting factors and summed (as per the Activity Function discussed above) to create the composite QRS complex 220. It can be seen from the composite QRS complex (i.e., Activity Function) that the composite QRS complex has been formed, in equal parts, by the "weak" signals illustrated in FIG. 2. Thus, FIG. 2 shows pictographically that the present invention weights all signals equally when it is determined that no signal is significantly "better" than another.

The preceding dealt with the first special case checked. The second special case to be checked for is that where there is at least one good quality lead, and possibly one or more weak (low amplitude) leads. In such a case, the SQI of the weak leads will be set equal to zero, while the SQI of the leads that did not fit the weak lead criterion would be calculated as normally utilizing the SQI equation given above.

In one illustrative embodiment, the explicit criteria by which it is determined if there is at least one good quality lead, and one or more weak (low amplitude) leads is as follows:

if (MAX{SQI$^{(i)}$, i=1,...N}>3)
 THEN
  for all other leads,
   (set SQI$^{(i)}$=0 where the following condition
   is true: (MAX{|V$^{(i)}$(j)|,j=n-49,...n}<300μV) otherwise
   calculate SQI$^{(i)}$ in the normal fashion)

where:

SQI$^{(i)}$ is the signal quality index calculated for lead i;

i is a lead under consideration, and ranges from 1 to N where N is the total number of leads present;

j is the jth EKG data sample for lead i under consideration;

n is the leading edge sample time of the sample window over which SQI is computed (width of sample window is 50 samples, in the equation given); and V$^{(i)}$(j) is the EKG value at the jth data sample for the ith lead.

In words, the equations state that if at least one lead had a calculated SQI greater than 3, and at least one lead had a maximum sampled value less than or equal to 300 microvolts, then set the SQI for the leads in which the maximum sampled value of the signal was less than or equal to 300 microvolts to be zero. Otherwise, calculate the SQI for the remaining leads utilizing the SQI equation set forth above.

Figure 3:
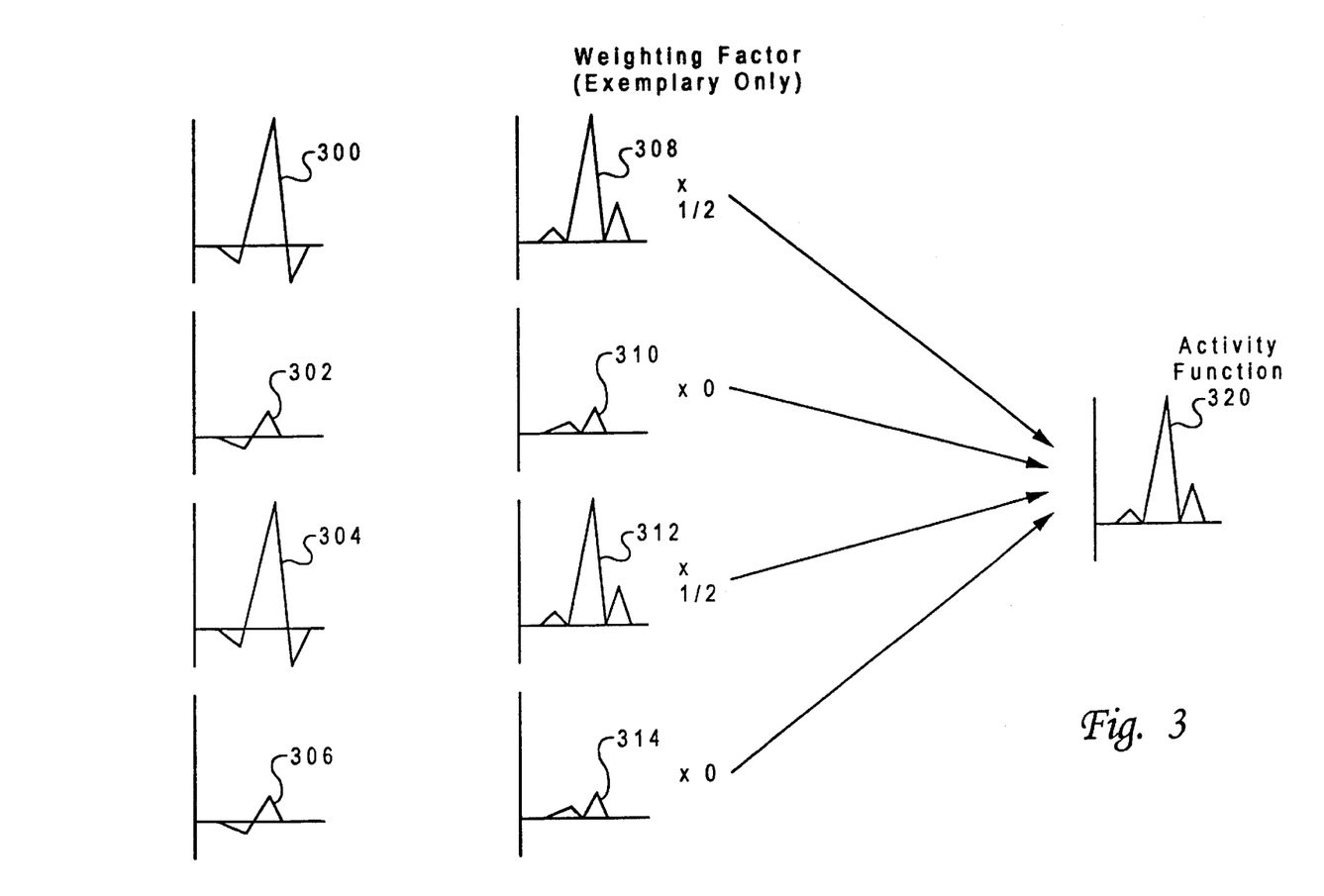
FIG. 3 is a partially schematic diagram illustrating concepts involved in a second special case.

Refer now to FIG. 3, which is a partially schematic diagram illustrating concepts involved in the special case just referenced. Shown in FIG. 3 are four exemplary electrocardiographic signals (leads). Electrocardiographic signals 300, 302, 304, and 306 are all QRS complexes. Shown are that electrocardiographic signals 302 and 306 have magnitudes much less than and are of much worse shape than electrocardiographic signals 300 and 304.

The Activity Function utilizes the absolute value of electrocardiographic signals. Accordingly, shown in FIG. 3 are rectified versions 308, 310, 312, and 314 of the four electrocardiographic signals 300, 302, 304, and 306, respectively.

As has been discussed above, in the special case shown in FIG. 3, where at least one electrocardiographic signal is found to be "good" and where one or more electrocardiographic signals are found to be "weak," the SQI for each such "weak" lead is assigned a value of zero. Accordingly, the SQI for all leads present is calculated utilizing the SQI equation set forth above.

In the situation shown in FIG. 3, electrocardiographic signals 300 and 304 are "good." Therefore, for the sake of illustration, it is assumed that when SQIs for electrocardiographic signals 300 and 304 are calculated utilizing the standard SQI formula set forth above, the SQIs for each will both be in excess of whatever first threshold value is relevant (e.g., 3 in the specific equation set forth above). Thereafter, the signal strength on all leads is compared to the second relevant threshold value (e.g., 300 microvolts in the specific equation set forth above). For those leads with signal strength less than or equal to the second relevant threshold, the signal is deemed "weak" and the SQI for such leads is accordingly set to zero.

Thereafter, the standard weighting factor equation set forth above is utilized to assign a weighting factor to all leads; inspection of the standard weighting function equation shows that if an SQI of a lead is zero, then the weight for that lead will also be zero. Accordingly, shown in FIG. 3 is that rectified QRS complexes 310 and 314 are assigned weighting factors of zero (since the SQI of such "weak" leads has been defined to be zero). Furthermore, shown in FIG. 3 is that rectified QRS complexes 308, and 312 (equating to QRS complexes 300, and 304, respectively) are each assigned weighting factors of ½, since there are two leads remaining and that each remaining lead has an equally good signal and hence SQI index (the weighting factors shown herein are merely presented to illustrate the concepts involved, and are not actual weighting functions derived from the signals shown).

The rectified QRS complexes shown are then all multiplied by their respective weighting factors and summed (as per the Activity Function discussed above) to create the composite QRS complex 320. It can be seen from the composite QRS complex (i.e., Activity Function) that the composite QRS complex has been formed, in equal parts, by the "strong" signals illustrated in FIG. 3 and that the contribution of the "weak" signals have been disregarded. Thus, FIG. 3 shows pictographically that the present invention effectively eliminates the contribution, of signals deemed to be excessively "weak" signals, to the Activity Function.

The preceding dealt with the second special case checked. The third special case that is checked for is that where "running averages" of low frequency noise and high frequency noise within one or more leads indicate that such leads are inherently unreliable, in which case the SQI of such inherently unreliable reads is set to equal zero, thereby effectively removing them from appearing in the construction of the "Activity Function."

The "running average" for the high frequency noise is known as the "high frequency noise index" and is defined in the present invention by the following equation which is updated at a time sample subsequent to the detection of a QRS complex:

$$\overline{HFNI^{(i)}}(j) = \overline{HFNI^{(i)}}(j-1) + \tfrac{1}{\alpha}[HFNI^{(i)}(j) - \overline{HFNI^{(i)}}(j-1)]$$

where $\alpha = 4$ if $HFNI^{(i)}(j) \geq \overline{HFNI^{(i)}}(j-1)$ $\alpha = 8$ if $HFNI^{(i)}(j) < \overline{HFNI^{(i)}}(j-1)$ and where:
- i is a lead under consideration, and ranges from 1 to N where N is the total number of leads present;
- j is the jth EKG data sample for lead i under consideration;
- $HFNI^{(i)}$ quantities without the over-bar refer to the current (via the $HFNI^{(i)}$ without the over-bar equation defined later) high frequency noise index values; and
- $HFNI^{(i)}$ quantities with the over-bar refer to the running average of the high frequency noise index.

As has been stated, if the "running average" of the high frequency noise indicates that a lead is inherently unreliable, such a lead is removed from the composition that ultimately forms the Activity Function. In the present invention, the determination of whether the "running average" indicates unreliability is determined by the following:

if $\overline{HFNI^{(i)}}(j) > \epsilon_{HF}$ set $SQI^{(i)} = 0$ where $\epsilon_{HF} = MAX\{3MIN[\overline{HFNI^{(i)}}(j), i=1, \ldots N], 800\}$ The "running average" for the low frequency noise is known as the "low frequency noise index" and is defined in the present invention by the following equation which is updated at a time sample subsequent to the detection of a QRS complex:

$$\overline{LFNI^{(i)}}(j) = \overline{LFNI^{(i)}}(j-1) + \tfrac{1}{\alpha}[LFNI^{(i)}(j) - \overline{LFNI^{(i)}}(j-1)]$$

where
- $\alpha = 4$ if $LFNI^{(i)}(j) \geq \overline{LFNI^{(i)}}(j-1)$
- $\alpha = 8$ if $LFNI^{(i)}(j) < \overline{LFNI^{(i)}}(j-1)$ and where:
- i is a lead under consideration, and ranges from 1 to N where N is the total number of leads present;
- j is the jth EKG data sample for lead i under consideration;
- $LFNI^{(i)}$ quantities without the over-bar refer to the current calculated (via the $LFNI^{(i)}$ without the over-bar equation defined later) low frequency noise index value; and
- $LFNI^{(i)}$ quantities with the over-bar refer to the running average low frequency noise index.

As has been stated, if the "running average" of the low frequency noise indicates that a lead is inherently unreliable, such a lead is removed from the composition that ultimately forms the Activity Function. In the present invention, the determination of whether the "running average" indicates unreliability is determined by the following:

if $\overline{LFNI^{(i)}}(j) > \epsilon_{LF}$ set $SQI^{(i)} = 0$ where $\epsilon_{LF} = MAX\{3MIN[\overline{LFNI^{(i)}}(j), i=1, \ldots N], 800\}$ The foregoing equations for calculating running averages utilize high and low frequency noise measurement. In the present invention, the high and low frequency measurements are obtained from the electrocardiographic leads as follows.

The high frequency noise index is computed as a ratio of high frequency noise to signal. In order to obtain the high frequency noise the input EKG signal V(j) is high pass filtered using a 2nd difference filter which is computed as follows on a sample by sample basis:

$$X^{(i)}(j) = V^{(i)}(j+1) - 2V^{(i)}(j-1)$$

and the high frequency noise index is computed as follows upon the detection of a QRS complex:

$$HFNI^{(i)}(k) = \frac{\sum_{j=k-62}^{k+62} |X^{(i)}(j)|}{RHT_k^{(i)}}$$

where:
- i is a lead under consideration, and ranges from 1 to N where N is the total number of leads present;
- j is the jth EKG data sample for lead i under consideration;
- $V^{(i)}(j)$ is the EKG value at the jth data sample for the ith lead;
- $RHT_k^{(i)}$ equals the absolute value of the amplitude of the R-wave detected at the kth sample of the ith lead;
- summation is over 125 8 millisecond intervals centered at the R-wave; and
- $X^{(i)}(j)$ is the high pass filtered output.

The low frequency noise index is computed as a ratio of low frequency noise to signal. In order to obtain the low frequency noise the input EKG signal V(j) is low pass filtered using the following equation which is computed on a sample by sample basis:

$$Y^{(i)}(j) = Y^{(i)}(j-1) + \tfrac{1}{16}[V^{(i)}(j) - Y^{(i)}(j-1)]$$

and the low frequency noise index is computed as follows upon the detection of a QRS complex:

$$LFNI^{(i)}(k) = \frac{\sum_{j=k-62}^{k+62} |Y^{(i)}(j)|}{RHT_k^{(i)}}$$

where:
- i is a lead under consideration, and ranges from 1 to N where N is the total number of leads present;
- j is the jth EKG data sample for lead i under consideration;
- $V^{(i)}(j)$ is the EKG value at the jth data sample for the ith lead;
- $RHT_k^{(i)}$ equals the absolute value of the amplitude of the R-wave detected at the kth sample of the ith lead;
- summation is over 125 8 millisecond intervals centered at the R-wave; and
- $Y^{(i)}(j)$ is the low pass filtered output.

Figure 4:
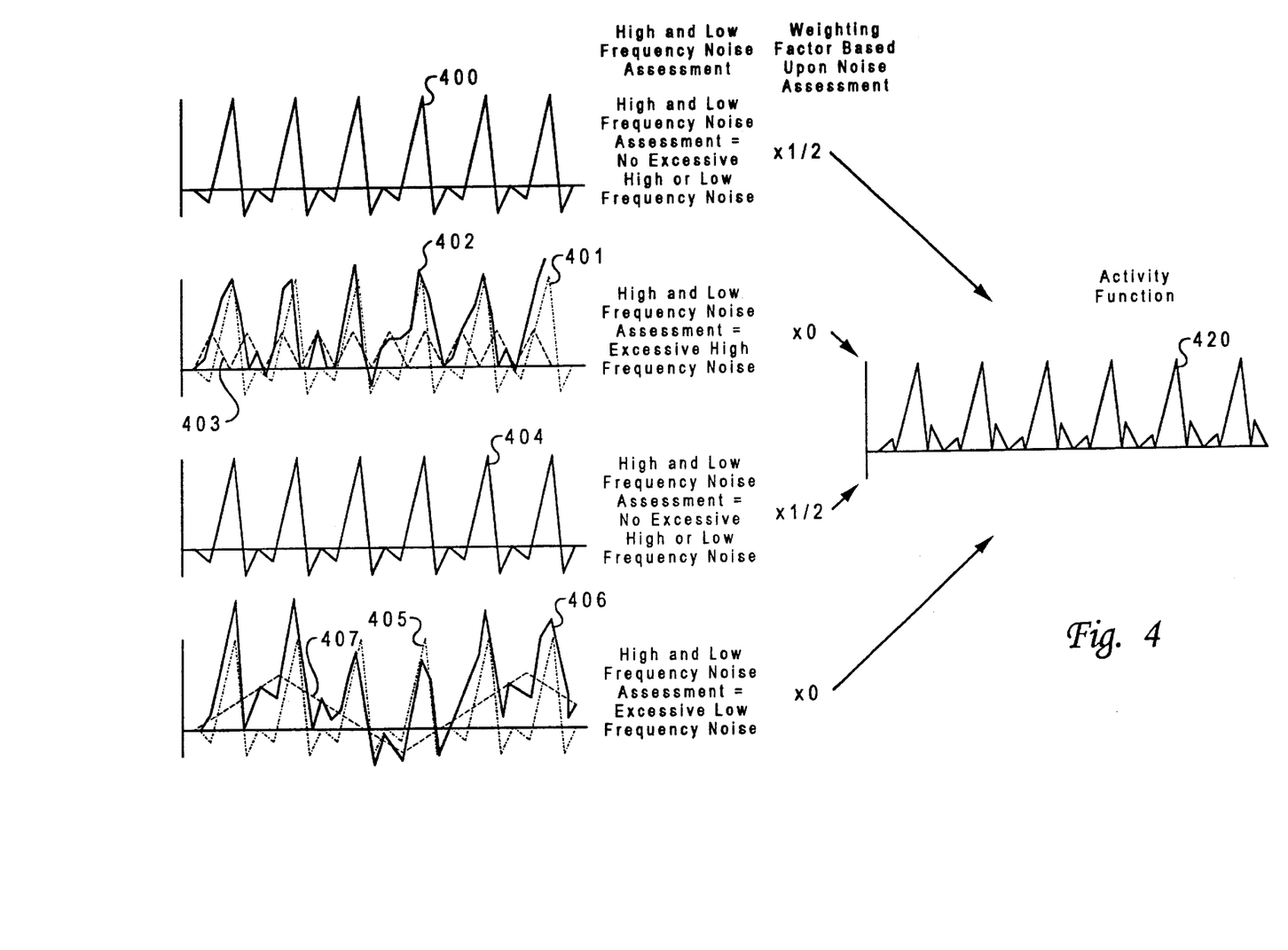
FIG. 4 is a partially schematic diagram illustrating concepts involved in a third special case.

Refer now to FIG. 4, which is a partially schematic diagram illustrating concepts involved in the special case just referenced, where two of the signals shown are acceptable, while one of signals shown has excessive high frequency noise and another of the signals shown has excessive low frequency noise. Shown in FIG. 4 are four exemplary electrocardiographic signals (leads). Electrocardiographic signals 400, 402, 404, and 406 all manifest QRS complexes.

Shown are that electrocardiographic signals 402 and 406 which have significant high frequency noise components and low frequency noise components, respectively. Shown is that electrocardiographic signal 402 is composed of a clean electrocardiographic waveform component 401 and a high frequency noise component 403. Also shown is that electrocardiographic 406 is composed of another clean electrocardiographic waveform component 405 and a low frequency component 407.

As has been discussed above, it is known that the Activity Function utilizes the absolute value of electrocardiographic signals. The same remains true here. However, in FIG. 4 the rectified versions of the electrocardiographic signals 400, 402, 404, and 406 are not shown, but it is to be understood that they are present.

As has been discussed above, in the special case shown in FIG. 4, where an electrocardiographic signal has either excessive high frequency or excessive low frequency noise, the SQI for each lead is assigned a value of zero. As has been discussed above, in the special case shown in FIG. 4, where one or more electrocardiographic signals are found to be excessively noisy, the SQI for each such "noisy" lead is assigned a value of zero. Subsequently, the SQI of all leads found not be noisy is calculated utilizing the SQI formula set forth above. Thereafter, the standard weighting factor equation set forth above is utilized to assign a weighting factor to all leads; inspection of the standard weighting function equation shows that if an SQI of a lead is zero, then the weight for that lead will also be zero.

It is shown in FIG. 4 that electrocardiographic signal 402 has been assessed to have excessive high frequency components. (In the present invention, as was discussed above, this is determined by the running average High Frequency Noise Index.) Accordingly, shown in FIG. 4 is that excessively noisy (due to excessive high frequency noise component 403) electrocardiographic signal 402 is assigned a weighting factor of zero (since the SQI of such an excessively noisy lead has been defined to be zero, and utilizing the weighting equation such results in a weighting factor of zero).

Also shown in FIG. 4 is that excessively noisy (due to excessive low frequency noise component 407) electrocardiographic signal 406 is assigned a weighting factors of zero (since the SQI of such an excessively noisy lead has been defined to be zero, and utilizing the weighting equation such results in a weighting factor of zero).

Furthermore, shown in FIG. 4 is that QRS complexes 400, and 406 are each assigned weighting factors of ½, since there are two leads remaining which have not been assigned an SQI of zero and that each remaining lead has an equally good signal and hence SQI index (the weighting factors shown herein are merely presented to illustrate the concepts involved, and are not actual weighting functions derived from the signals shown).

The QRS complexes (i.e., electrocardiographic signals) shown are then all multiplied by their respective weighting factors and summed (as per the Activity Function discussed above) to create the composite QRS complex 420. It can be seen from the composite QRS complex (i.e., Activity Function) that the composite QRS complex has been formed, in equal parts, by the "strong" signals illustrated in FIG. 4 and that the contribution of the excessively noisy signals have been disregarded. Thus, FIG. 4 shows pictographically that the present invention effectively eliminates the contribution of signals deemed to be excessively noisy signals to the Activity Function.

Figure 5A:
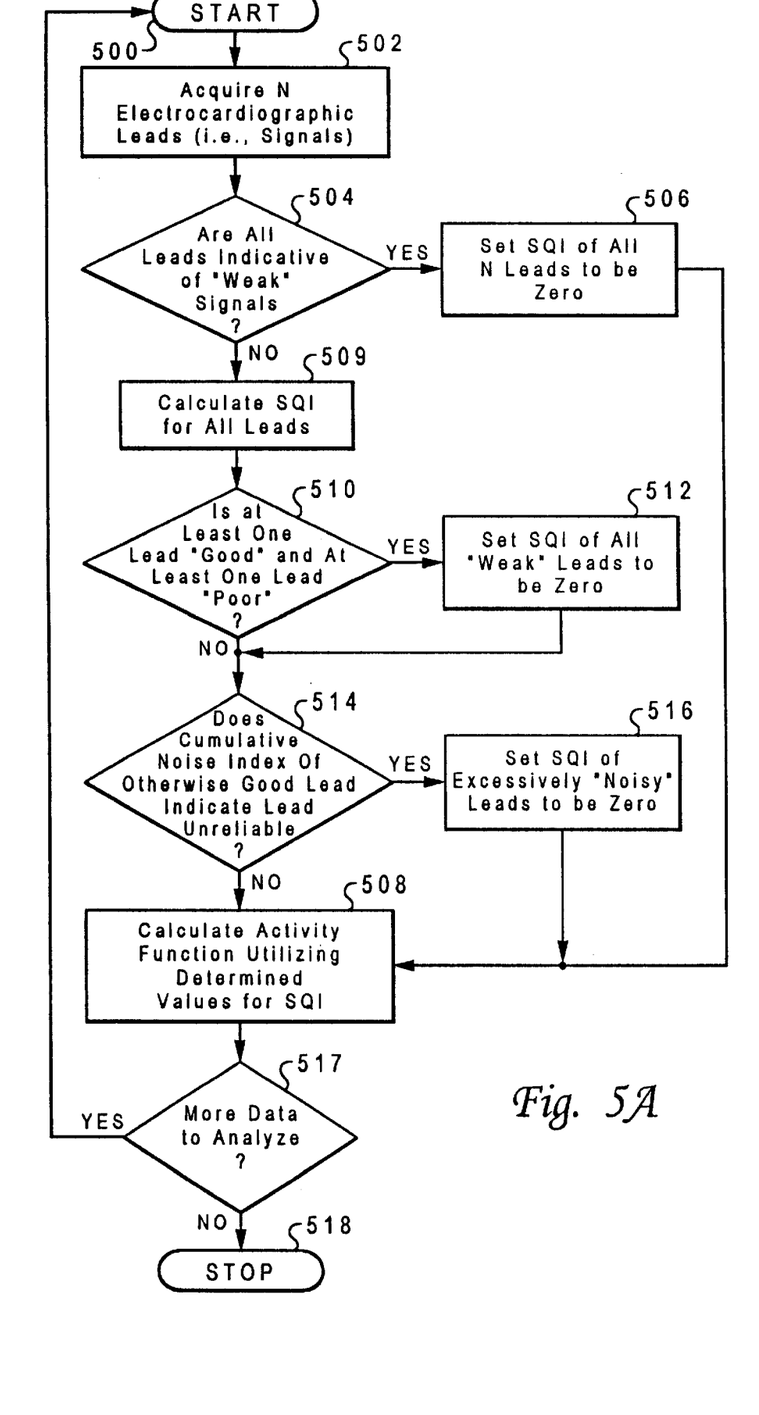
FIG. 5A is a high-level logic flowchart depicting the method and process of the present invention.

Refer now to FIG. 5A, which is a high-level logic flowchart depicting the method and process of the present invention. Method step 500 shows the start of the process. Method step 502 depicts the acquisition of N electrocardiographic leads (i.e., electrocardiographic signals).

Method step 504 illustrates the determination of whether all N leads are representative of "weak" signals (e.g., as was discussed above in relation to FIG. 2). If it is determined that all leads are "weak" signals, then the process proceeds to method step 506 wherein it is shown that the SQI of all N leads is set to zero. Thereafter, the process proceeds to method step 508 where the Activity Function is calculated utilizing the determined SQI values for each lead.

If it is determined that not all leads are "weak" signals, then the process proceeds to method step 509 which illustrates that the SQI for all leads is calculated. Thereafter, the process proceeds to method step 510 which illustrates the determination of whether at least one lead has a "good" signal and whether one or more leads are representative of "weak" signals (e.g., as was discussed above in relation to FIG. 3). If the criteria of method step 510 are not met, then the process proceeds to method step 514. If it is determined that at least one lead has a "good" signal (via use of the SQI values calculated in method step 509) and that one or more leads are "weak" (via use of the amplitude of those leads) signals, then the process proceeds to method step 512 wherein it is shown that the SQI of all "weak" leads is set to zero. Thereafter the process proceeds to method step 514.

Method step 514 illustrates the determination of whether one or more otherwise "good" or "strong" signals, should nevertheless be discarded in that a cumulative index of either or both the high and low frequency noise present in the lead indicate that the signal is inherently unreliable. In the event that it is determined that one or more otherwise "good" or "strong" signals is inherently unreliable due to noise, then the process proceeds to method step 516 which shows that the SQI for those excessively noisy channels is set to zero. Thereafter, the process proceeds to method step 508 which depicts the calculation of the Activity Function utilizing the determined SQI values for each lead.

If it is determined that none of the otherwise "good" or "strong" signals is inherently noisy, then the process proceeds to method step 508 which depicts the calculation of the Activity Function utilizing the determined SQI values for each lead.

Subsequent to method step 508 the process proceeds to method step 517 which illustrates a determination of whether more data to be analyzed exists. If more data to be analyzed exists, then the process proceeds to method step 502 and repeats. However, if no more data to be analyzed exists the process proceeds to method step 518 and stops.

Figure 5B:
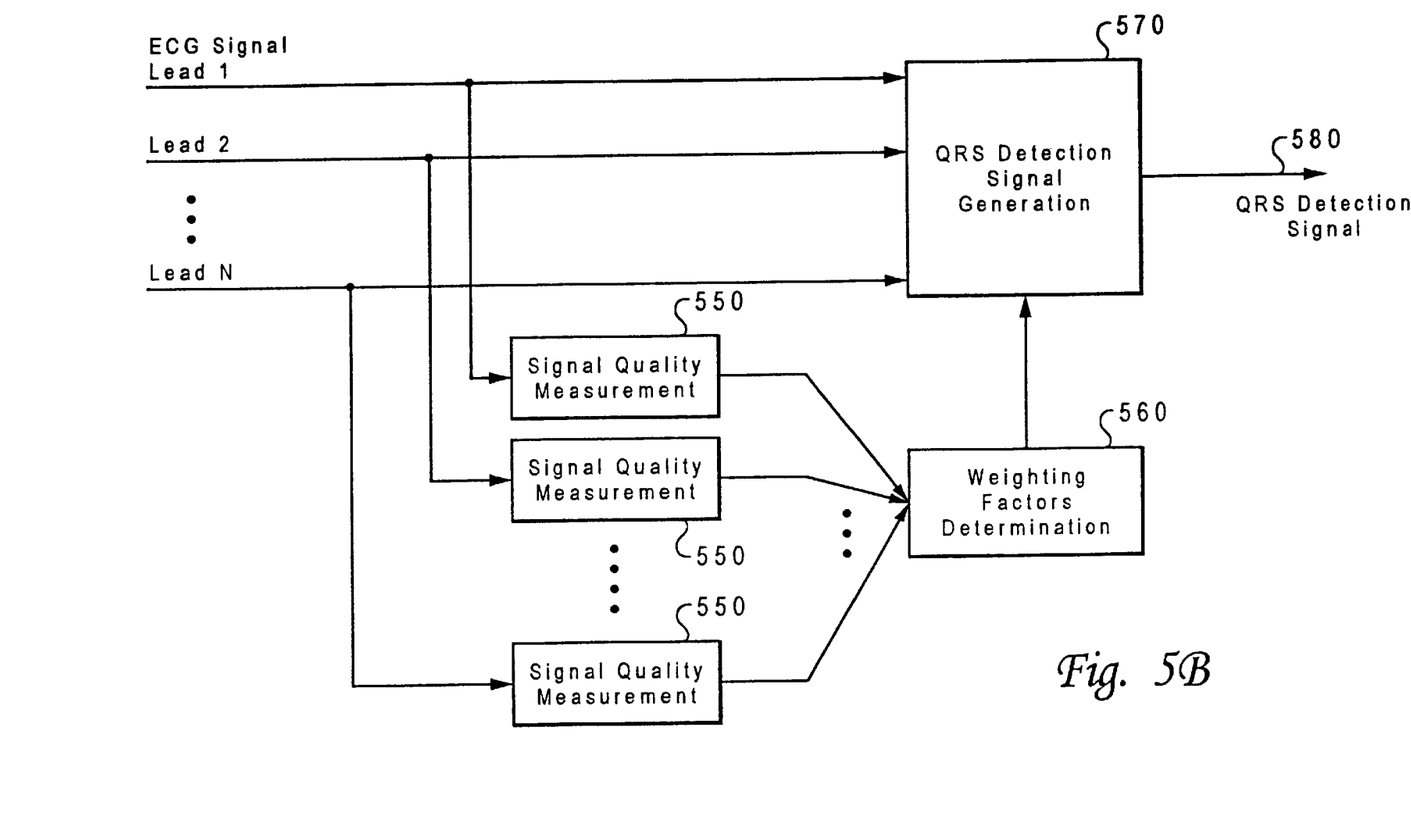
FIG. 5B is a partially schematic block diagram illustrative of a method and system for implementing the present invention.

Refer now to FIG. 5B, which is a partially schematic block diagram illustrative of a method and system for implementing the present invention. Shown in FIG. 5B are EKG Leads (or channels, or signals) 1 through N (as have been discussed previously in relation to the foregoing equations and figures). Shown is that each lead is fed into a corresponding Signal Quality Measurement Block 550. Each Signal Quality Measurement Block 550 will calculate the SQI for each lead utilizing the differing and various formulas and special case SQI inquires set forward earlier in this application. Those skilled in the art will recognize that there are various ways that each Signal Quality Measurement Block 550 could be implemented, such as in software, hardware, firmware, or any combination of the foregoing.

FIG. 5B depicts that subsequent to the determination of SQI for each lead by each Signal Quality Measurement Block 550, such SQIs are fed into Weighting Factors Determination Block 560. Weighting Factors Determination Block 560 will calculate the Weighting Factor for each lead (or channel, or signal) utilizing the differing and various formulas and special case inquires set forward earlier in this application. Those skilled in the art will recognize that there are various ways that Weighting Factors Determination Block 560 could be implemented, such as in software, hardware, firmware, or any combination of the foregoing.

Subsequent to the determination of weighting factors appropriate to each lead (or channel, or signal), such weighting factors are illustrated as being fed into QRS Detection Signal Generation Block 570 which utilizes such weighting factors in conjunction with the Activity Function set forth previously in order to calculate and produce the output of the Activity function for EKG Leads 1 through N. This output is denoted in FIG. 5B as QRS Detection Signal 580. Those skilled in the art will recognize that there are various ways that QRS Detection Signal Generation Block 570 could be implemented, such as in software, hardware, firmware, or any combination of the foregoing.

Figure 6:
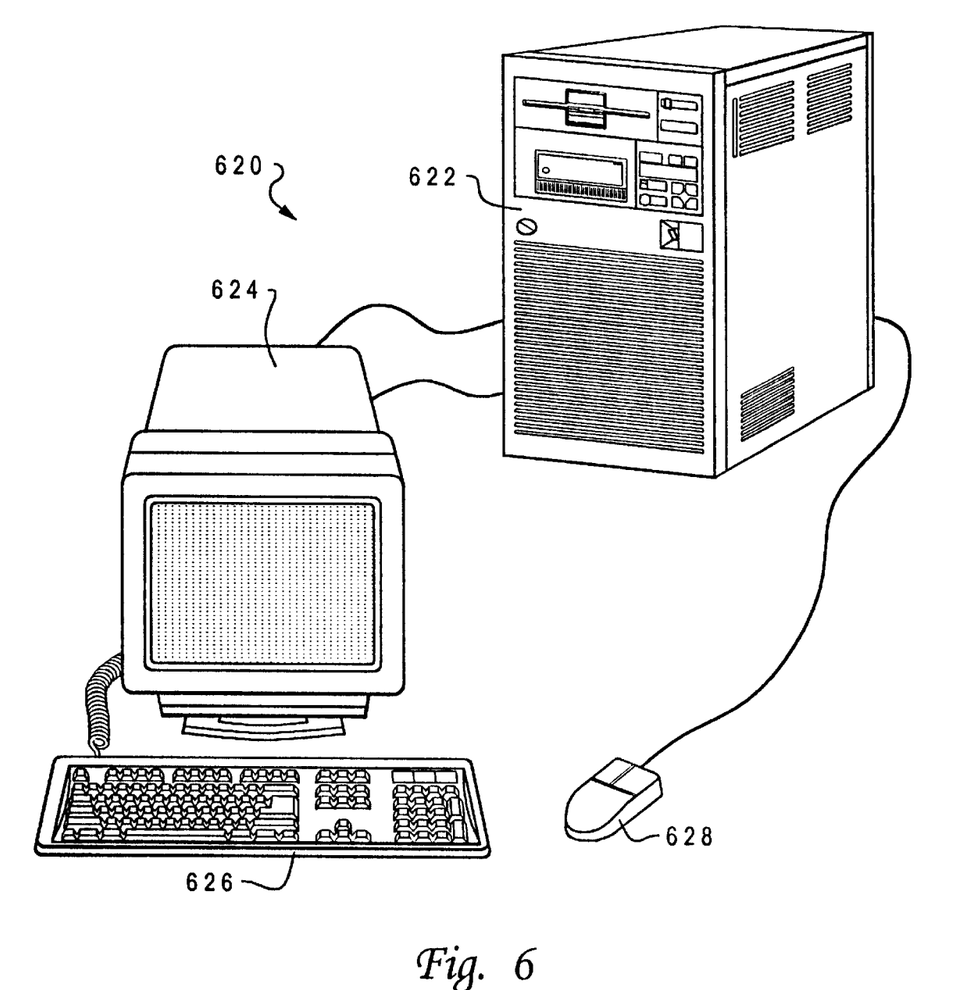
FIG. 6 depicts a pictorial representation of a data-processing system which can be utilized in accordance with the method and system of an illustrative embodiment of the present invention.

With reference now to the figures and in particular with reference now to FIG. 6, there is depicted a pictorial representation of a data-processing system which can be utilized in accordance with the method and system of an illustrative embodiment of the present invention. The method and system provided by an illustrative embodiment of the present invention can be implemented with the data-processing system depicted in FIG. 6. A computer 620 is depicted which includes a system unit 622, a video display terminal 624, a keyboard 626, and a mouse 628. Computer 620 may be implemented utilizing any suitably powerful computer, such as commercially available mainframe computers, minicomputers, or microcomputers.

Figure 7:
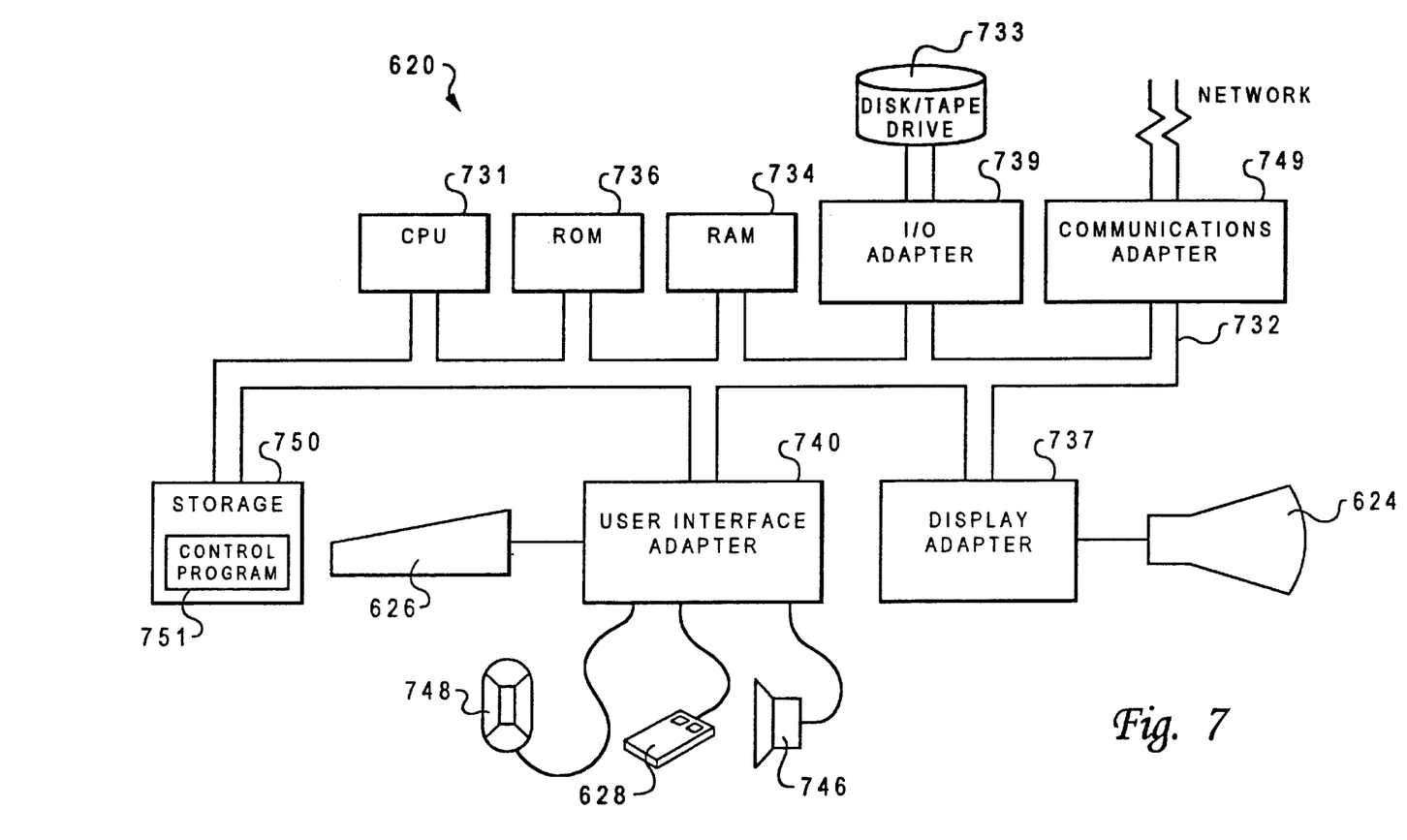
FIG. 7 is an illustration of a representative hardware environment which can be utilized in accordance with the method and system of an illustrative embodiment of the present invention.

FIG. 7 is an illustration of a representative hardware environment which can be utilized in accordance with the method and system of an illustrative embodiment of the present invention. FIG. 7 depicts selected components in computer 620 in which an illustrative embodiment of the present invention may be implemented. System unit 622 includes a Central Processing Unit ("CPU") 731, such as a conventional microprocessor, and a number of other units interconnected via system bus 732. Computer 620 includes random-access memory ("RAM") 734, read-only memory ("ROM") 736, display adapter 737 for connecting system bus 732 to video display terminal 624, and I/O adapter 739 for connecting peripheral devices (e.g., disk and tape drives 733) to system bus 732. Video display terminal 624 is the visual output of computer 620, which can be a CRT-based video display well-known in the art of computer hardware. However, with a portable or notebook-based computer, video display terminal 624 can be replaced with an LCD-based or a gas plasma-based flat-panel display. Computer 620 further includes user interface adapter 740 for connecting keyboard 626, mouse 628, speaker 746, microphone 748, and/or other user interface devices, such as a touch screen device (not shown), to system bus 732. Communications adapter 749 connects computer 620 to a data-processing network.

Any suitable machine-readable media may retain the method and system of an illustrative embodiment of the present invention, such as RAM 734, ROM 736, a magnetic diskette, magnetic tape, or optical disk (the last three being located in disk and tape drives 733). Any suitable operating system and associated graphical user interface may direct CPU 731. Other technologies can also be utilized in conjunction with CPU 731, such as touch-screen technology or human voice control. In addition, computer 620 includes a control program 751 which resides within computer storage 750. Control program 751 contains instructions that when executed on CPU 731 carries out the operations depicted in the logic flowchart of FIG. 5A and the partially schematic diagrams of FIGS. 1, 2, 3, 4, and 5B as described herein.

Those skilled in the art will appreciate that the hardware depicted in FIG. 7 may vary for specific applications. For example, other peripheral devices such as optical disk media, audio adapters, or chip programming devices, such as PAL or EPROM programming devices well-known in the art of computer hardware, and the like may be utilized in addition to or in place of the hardware already depicted.

As a final matter, it is important that while an illustrative embodiment of the present invention has been, and will continue to be, described in the context of a fully functional computing system, those skilled in the art will appreciate that the mechanisms of an illustrative embodiment of the present invention are capable of being distributed as a program product in a variety of forms, and that an illustrative embodiment of the present invention applies equally regardless of the particular type of signal bearing media used to actually carry out the distribution. Examples of signal bearing media include recordable type media such as floppy disks, hard disk drives, CD ROMs, and transmission type media such as digital and analogue communication links.

While an illustrative embodiment has been particularly shown and described, it will be understood by those skilled in the art that various changes in form and detail may be made therein without departing from the spirit and scope of the illustrative embodiment.

What is claimed is:

1. A method for characterizing the quality of signals indicative of heart function, where such signals indicative of heart function are derived from electrocardiographic measurements, said method comprising the steps of:

measuring one or more signals indicative of heart function;

sampling at a cardinal number of points each of said measured one or more signals;

determining, for each of said sampled one or more signals, a maximum sampled value that occurred over said cardinal number of sample points; and calculating, for each of said sampled one or more signals, a signal quality index by dividing said determined maximum value by a divisor associated with each of said sampled one or more signals.

2. The method of claim 1 wherein said step of calculating a signal quality index further comprises the steps of:

calculating said divisor associated with each of said one or more sampled signals by summing, for each of said sampled one or more signals, each sampled value that was taken at each of said cardinal number of sample points.

3. The method of claim 1 wherein said step of calculating a signal quality index further comprises the steps of:

summing, for each of said sampled one or more signals, each sampled value that was taken at each of said cardinal number of sample points; and calculating said divisor associated with each of said one or more sampled signals by multiplying the results of said summing step by the reciprocal of the number of cardinal points where said sampling occurred.

4. A method for providing highly accurate characterizations of waveform representations of heart function, where such waveform representations are derived from electrocardiographic measurements, said method comprising the steps of:

measuring one or more signals indicative of heart function;

calculating a signal quality index for each of said measured one or more signals indicative of heart function;

calculating one or more weighting factors dependent upon said calculated signal quality index for each of said one or more measured signals indicative of heart function; and creating a waveform representation comprised of each of said one or more measured signals indicative of heart function multiplied by said calculated weighting factor corresponding to said each of said one or more measured signals indicative of heart function.

5. The method of claim 4, wherein said step of calculating a signal quality index further comprises the steps of:

measuring one or more signals indicative of heart function;

sampling at a cardinal number of points each of said measured one or more signals;

determining, for each of said sampled one or more signals, a maximum sampled value that occurred over said cardinal number of sample points; and calculating, for each of said sampled one or more signals, said signal quality index by dividing said determined maximum value by a divisor associated with each of said sampled one or more signals.

6. The method of claim 5 wherein said step of calculating said signal quality index further comprises the steps of:

calculating said divisor associated with each of said one or more sampled signals by summing, for each of said sampled one or more signals, each sampled value that was taken at each of said cardinal number of sample points.

7. The method of claim 5 wherein said step of calculating said signal quality index further comprises the steps of:

summing, for each of said sampled one or more signals, each sampled value that was taken at each of said cardinal number of sample points; and calculating said divisor associated with each of said one or more sampled signals by multiplying the results of said summing step by the reciprocal of the number of cardinal points where said sampling occurred.

8. The method of claim 4 wherein said step of calculating one or more weighting factors further comprises the steps of:

summing said calculated signal quality index for each of said one or more measured signals indicative of heart function;

comparing said sum of said calculated signal quality index for each of said one or more measure signals to zero;

in response to said comparing step indicating that said sum of said calculated signal quality indexes is equal to zero, calculating said one or more weighting factors to all be equal to the number one divided by the total aggregate number of said measured one or more signals; and in response to said comparing step indicating that said sum of said calculated signal quality index for each of said one or more signals is not equal to zero, calculating said one or more weighting factors for each of said one or more measured signals by dividing said signal quality index for each of said one or more signals by the result of said summing step.

9. The method of claim 4 wherein said step of calculating one or more weighting factors further comprises the steps of:

adjusting said calculated signal quality indexes in special case instances;

summing said calculated signal quality index for each of said one or more measured signals indicative of heart function;

comparing said sum of said calculated signal quality index for each of said one or more measure signals to zero;

in response to said comparing step indicating that said sum of said calculated signal quality indexes is equal to zero, calculating said one or more weighting factors to all be equal to the number one divided by the total aggregate number of said measured one or more signals; and in response to said comparing step indicating that said sum of said calculated signal quality index for each of said one or more signals is not equal to zero, calculating said one or more weighting factors for each of said one or more measured signals by dividing said signal quality index for each of said one or more signals by the result of said summing step.

10. The method of claim 9 wherein said step of adjusting said calculated signal quality indexes in special case instances further comprises the steps of:

sampling at a cardinal number of points each of said measured one or more signals;

determining a maximum sampled value of each of said measured one or more signals that occurred over said cardinal number of sample points;

comparing said determined maximum sampled value of each of said measured one or more signals to a prespecified threshold; and in response to such comparing step showing that all of said determined maximum sampled values are less than or equal to said prespecified threshold, calculating said signal quality index for each of said measured one or more signals to be equal to zero.

11. The method of claim 9 wherein said step of adjusting said calculated signal quality indexes in special case instances further comprises the steps of:

comparing said calculated signal quality index for each of said measured one or more signals to a first prespecified threshold; and in response to said comparing step showing that at least one of said calculated signal quality index for each of said measured one or more signals was above said first prespecified threshold:

setting equal to zero the signal quality index for each of said one or more measured signals whose determined maximum value was less than or equal to a second prespecified threshold provided that said each of said one of or more measured signals was not previously found to be the maximum signal quality index; and utilizing said calculated signal quality index for each of said measured one or more signals for each of said measured one or more signals whose signal quality index has not previously been set equal to zero.

12. The method of claim 9 wherein said step of adjusting said calculated signal quality indexes in special case instances further comprises the steps of:

maintaining a running average of high frequency noise within each one of said measured one or more signals;

maintaining a running average of low frequency noise within each one of said measured one or more signals;

comparing said maintained running average of high frequency noise within each of said measured one or more signals to a first calculated threshold;

comparing said maintained running average of low frequency noise within each of said measured one or more signals to a second calculated threshold; and setting equal to zero the calculated signal quality index for any of said measured one or more signals where said comparing steps demonstrated for said any of said measured one or more signals either that said maintained running average of low frequency noise exceeded said first computed threshold or that said maintained running average of high frequency noise exceeded said second computed threshold.

13. A system for characterizing the quality of signals indicative of heart function, where such signals indicative of heart function are derived from electrocardiographic measurements, said system comprising:

means for measuring one or more signals indicative of heart function;

means for sampling at a cardinal number of points each of said measured one or more signals;

means for determining, for each of said sampled one or more signals, a maximum sampled value that occurred over said cardinal number of sample points; and means for calculating, for each of said sampled one or more signals, a signal quality index by dividing said determined maximum value by a divisor associated with each of said sampled one or more signals.

14. The system of claim 13 wherein said means for calculating a signal quality index further comprises:

means for calculating said divisor associated with each of said one or more sampled signals by summing, for each of said sampled one or more signals, each sampled value that was taken at each of said cardinal number of sample points.

15. The system of claim 13 wherein said means for calculating a signal quality index further comprises:

means for summing, for each of said sampled one or more signals, each sampled value that was taken at each of said cardinal number of sample points; and means for calculating said divisor associated with each of said one or more sampled signals by multiplying the results of said summing step by the reciprocal of the number of cardinal points where said sampling occurred.

16. A system for providing highly accurate characterizations of waveform representations of heart function, where such waveform representations are derived from electrocardiographic measurements, said system comprising:

means for measuring one or more signals indicative of heart function;

means for calculating a signal quality index for each of said measured one or more signals indicative of heart function;

means for calculating one or more weighting factors dependent upon said calculated signal quality index for each of said one or more measured signals indicative of heart function; and means for creating a waveform representation comprised of each of said one or more measured signals indicative of heart function multiplied by said calculated weighting factor corresponding to said each of said one or more measured signals indicative of heart function.

17. The system of claim 16, wherein said means for calculating a signal quality index further comprises:

means for measuring one or more signals indicative of heart function;

means for sampling at a cardinal number of points each of said measured one or more signals;

means for determining, for each of said sampled one or more signals, a maximum sampled value that occurred over said cardinal number of sample points; and means for calculating, for each of said sampled one or more signals, said signal quality index by dividing said determined maximum value by a divisor associated with each of said sampled one or more signals.

18. The system of claim 17 wherein said means for calculating said signal quality index further comprises:

means for calculating said divisor associated with each of said one or more sampled signals by summing, for each of said sampled one or more signals, each sampled value that was taken at each of said cardinal number of sample points.

19. The system of claim 16 wherein said means for calculating said signal quality index further comprises:

means for summing, for each of said sampled one or more signals, each sampled value that was taken at each of said cardinal number of sample points; and means for calculating said divisor associated with each of said one or more sampled signals by multiplying the results of said summing step by the reciprocal of the number of cardinal points where said sampling occurred.

20. The system of claim 16 wherein said means for calculating one or more weighting factors further comprises:

means for summing said calculated signal quality index for each of said one or more measured signals indicative of heart function;

means for comparing said sum of said calculated signal quality index for each of said one or more measure signals to zero;

means, responsive to said means for comparing indicating that said sum of said calculated signal quality indexes is equal to zero, for calculating said one or more weighting factors to all be equal to the number one divided by the total aggregate number of said measured one or more signals; and means, responsive to said means for comparing indicating that said sum of said calculated signal quality index for each of said one or more signals is not equal to zero, for calculating said one or more weighting factors for each of said one or more measured signals by dividing said signal quality index for each of said one or more signals by the resultant of said means for summing.

21. The system of claim 16 wherein said means for calculating one or more weighting factors further comprises:

means for adjusting said calculated signal quality indexes in special case instances;

means for summing said calculated signal quality index for each of said one or more measured signals indicative of heart function;

means for comparing said sum of said calculated signal quality index for each of said one or more measure signals to zero;

means, responsive to said means for comparing indicating that said sum of said calculated signal quality indexes is equal to zero, for calculating said one or more weighting factors to all be equal to the number one divided by the total aggregate number of said measured one or more signals; and means, responsive to said means for comparing indicating that said sum of said calculated signal quality index for each of said one or more signals is not equal to zero, for calculating said one or more weighting factors for each of said one or more measured signals by dividing said signal quality index for each of said one or more signals by the resultant of said means for summing.

22. The system of claim 21 wherein said means for adjusting said calculated signal quality indexes in special case instances further comprises:

means for sampling at a cardinal number of points each of said measured one or more signals;

means for determining a maximum sampled value of each of said measured one or more signals that occurred over said cardinal number of sample points;

means for comparing said determined maximum sampled value of each of said measured one or more signals to a prespecified threshold; and means, responsive to such means for comparing showing that all of said determined maximum sampled values are less than or equal to said prespecified threshold, for calculating said signal quality index for each of said measured one or more signals to be equal to zero.

23. The system of claim 21 wherein said means for adjusting said calculated signal quality indexes in special case instances further comprises:

means for comparing said calculated signal quality index for each of said measured one or more signals to a first prespecified threshold; and means, responsive to said means for comparing showing that at least one of said calculated signal quality index for each of said measured one or more signals was above said first prespecified threshold:

for setting equal to zero the signal quality index for each of said one or more measured signals whose determined maximum value was less than or equal to a second prespecified threshold provided that said each of said one of or more measured signals was not previously found to be the maximum signal quality index; and for utilizing said calculated signal quality index for each of said measured one or more signals for each of said measured one or more signals whose signal quality index has not previously been set equal to zero.

24. The system of claim 21 wherein said means for adjusting said calculated signal quality indexes in special case instances further comprises:

means for maintaining a running average of high frequency noise within each one of said measured one or more signals;

means for maintaining a running average of low frequency noise within each one of said measured one or more signals;

means for comparing said maintained running average of high frequency noise within each of said measured one or more signals to a first calculated threshold;

means for comparing said maintained running average of low frequency noise within each of said measured one or more signals to a second calculated threshold; and means for setting equal to zero the calculated signal quality index for any of said measured one or more signals where said comparing steps demonstrated for said any of said measured one or more signals either that said maintained running average of low frequency noise exceeded said first computed threshold or that said maintained running average of high frequency noise exceeded said second computed threshold.

\* \* \* \* \*